United States Patent
Kaya

(10) Patent No.: US 9,551,662 B2
(45) Date of Patent: Jan. 24, 2017

(54) SURFACE PLASMON-FIELD ENHANCED FLUORESCENCE MEASUREMENT DEVICE AND FLUORESCENCE DETECTION METHOD USING THE SAME

(75) Inventor: Takatoshi Kaya, Inagi (JP)

(73) Assignee: KONICA MINOLTA, INC, Tokyo (JP)

(*) Notice: Subject to any disclaimer, the term of this patent is extended or adjusted under 35 U.S.C. 154(b) by 222 days.

(21) Appl. No.: 14/118,341

(22) PCT Filed: Apr. 23, 2012

(86) PCT No.: PCT/JP2012/060814
§ 371 (c)(1),
(2), (4) Date: Nov. 18, 2013

(87) PCT Pub. No.: WO2012/157403
PCT Pub. Date: Nov. 22, 2012

(65) Prior Publication Data
US 2014/0061506 A1    Mar. 6, 2014

(30) Foreign Application Priority Data
May 19, 2011 (JP) .................... 2011-112365

(51) Int. Cl.
*G01N 21/64* (2006.01)
(52) U.S. Cl.
CPC ........ *G01N 21/6428* (2013.01); *G01N 21/648* (2013.01); *G01N 21/6452* (2013.01)
(58) Field of Classification Search
CPC ............ G01N 21/6452; G01N 21/6428; G01N 21/648

USPC ................... 250/459.1, 458.1, 200
See application file for complete search history.

(56) References Cited

U.S. PATENT DOCUMENTS

| | | | |
|---|---|---|---|
| 2004/0197843 A1 | 10/2004 | Chou et al. | |
| 2009/0023202 A1* | 1/2009 | Narahara | G01N 21/6428 435/287.9 |
| 2009/0041630 A1 | 2/2009 | Hirabayashi | |
| 2009/0218516 A1 | 9/2009 | Gryczynski et al. | |
| 2009/0294692 A1* | 12/2009 | Bourke, Jr. | A23L 3/26 250/459.1 |
| 2012/0201716 A1 | 8/2012 | Matsuo | |

(Continued)

FOREIGN PATENT DOCUMENTS

| | | |
|---|---|---|
| JP | 2003-4629 A | 1/2003 |
| JP | 3743541 B2 | 2/2006 |

(Continued)

OTHER PUBLICATIONS

Extended European Search Report issued in connection with the corresponding Application No. 12785616.9-1554/2711689, PCT/JP2012060814; Date of Mailing: Dec. 5, 2014.

(Continued)

*Primary Examiner* — David Porta
*Assistant Examiner* — Gisselle Gutierrez
(74) *Attorney, Agent, or Firm* — Cantor Colburn LLP

(57) ABSTRACT

A surface plasmon-field enhanced fluorescence measurement device may be provided to accurately detect a specific substance even in the case in which a well member is used and achieving a simpler structure and a lower manufacturing cost, and a fluorescence detection method using the surface plasmon-field enhanced fluorescence measurement device.

13 Claims, 8 Drawing Sheets

(56) References Cited

U.S. PATENT DOCUMENTS

2014/0170024 A1* 6/2014 Fujimaki .............. G01N 21/553
422/69

FOREIGN PATENT DOCUMENTS

| JP | 2006-208069 A | 8/2006 | | |
|---|---|---|---|---|
| JP | 2007-3357 A | 1/2007 | | |
| JP | 2009-222484 A | 10/2009 | | |
| WO | 0034785 A1 | 6/2000 | | |
| WO | WO 2010134470 A1 * | 11/2010 | ........... | G01N 21/648 |
| WO | 2011/043202 A1 | 4/2011 | | |
| WO | WO 2013099871 A1 * | 7/2013 | ........... | G01N 21/648 |

OTHER PUBLICATIONS

Jakub Dostalek et al: Biosensors based on surface plasmon-enhanced fluorescence spectroscopy(Review) vol. 3, No. 3, Sep. 1, 2008, pp. FD12-FD22.
International Preliminary Report on Patentability for International Application No. PCT/JP2012/060814, issued Nov. 19, 2013, and Written Opinion for International Application No. PCT/JP2012/060814, mailed Jul. 7, 2012, with English translation.
International Search Report for International Application No. PCT/JP2012/060814, mailed Jul. 17, 2012.

* cited by examiner

Movement distance from a position of the center of gravity of a bottom surface region that is defined by a through hole of a well member (a)                              (b)

SURFACE PLASMON-FIELD ENHANCED FLUORESCENCE MEASUREMENT DEVICE AND FLUORESCENCE DETECTION METHOD USING THE SAME

This is the U.S. national stage of application No. PCT/JP2012/060814 filed on 23 Apr. 2012. Priority under 35 U.S.C. §119(a) and 35 U.S.C. §365(b) is claimed from Japanese Application No. 2011-112365, filed 19 May 2011, the disclosure of which is also incorporated herein by reference.

TECHNICAL FIELD

The present invention relates to a surface plasmon-field enhanced fluorescence measurement device and a fluorescence detection method using the surface plasmon-field enhanced fluorescence measurement device based on a principle of a surface plasmon excitation enhanced fluorescence spectroscopy (SPFS: Surface Plasmon-field enhanced Fluorescence Spectroscopy).

BACKGROUND ART

A surface plasmon resonance device (hereafter referred to as an SPR device) has been used in which a phenomenon for obtaining a high optical output by a resonance of an electron and a light in a minute region of a nanometer level or the like (a surface plasmon resonance (SPR: Surface Plasmon Resonance) phenomenon) is put to practical use and an extremely fine analyte in a biological body is detected for instance.

As shown in FIG. 12, the SPR device 100 is provided with a sensor structure 110 in which a metallic thin film 104 is formed on the top surface of a dielectric member 102 and a ligand containing layer 108 that includes a ligand immobilized region 106 is formed on the metallic thin film 104.

Moreover, the SPR device 100 is provided with a light source 114 that is configured to apply an excitation light 112 toward the metallic thin film 104 and a light receiving means 118 that is configured to receive a reflected light 116 that has been applied from the light source 114 and that has been reflected on the metallic thin film 104 on the side of the dielectric member 102 of the sensor structure 110.

In the case in which the SPR device 100 is used, a ligand is affixed to the ligand immobilized region 106 formed on the metallic thin film 104, and a sample solution that includes a specific analyte is supplied to that.

Moreover in this state, the excitation light 112 is applied at a resonance angle θ1 from the lower side of the dielectric member 102 to the metallic thin film 104, and the reflected light 116 that has been reflected on the metallic thin film 104 is received by the light receiving means 118.

In the case in which the excitation light 112 is applied at a resonance angle θ1 toward the metallic thin film 104, a crude density wave (a surface plasmon) is generated on the metallic thin film 104, and a coupling of the excitation light 112 and an electronic vibration in the metallic thin film 104 occurs, thereby causing a light amount of the reflected light 116 to be reduced.

For this phenomenon, a resonance angle θ1 is varied depending on an existence of an analyte. Consequently, by previously researching a resonance angle θ1 in the case in which a sample solution that does not include an analyte is supplied to the ligand immobilized region 106, it can be judged that a specific analyte is included in the case in which a resonance angle θ1 is different from a resonance angle θ1 at that time.

By this configuration, it can be judged whether or not a predetermined analyte is included in a sample solution.

On the other hand, a surface plasmon field enhanced fluorescence spectroscopic measurement device (hereafter referred to as an SPFS device) has also been developed in which the analyte detection can be carried out with a higher degree of accuracy as compared with the SPR device 100 based on a principle of a surface plasmon excitation enhanced fluorescence spectroscopy (SPFS: Surface Plasmon-field enhanced Fluorescence Spectroscopy) for putting a surface plasmon resonance (SPR) phenomenon to practical use.

As shown in FIG. 13, the SPFS device 200 is provided with a sensor structure 210 in which a metallic thin film 204 is formed on the top surface of a dielectric member 202 and a ligand containing layer 208 that includes a ligand immobilized region 206 is formed on the metallic thin film 204.

Moreover, the SPFS device 200 is provided with a light source 214 that is configured to apply an excitation light 212 toward the metallic thin film 204 and a light receiving means 218 that is configured to receive a reflected light 216 that has been applied from the light source 214 and that has been reflected on the metallic thin film 204 on the side of the dielectric member 202 of the sensor structure 210.

On the other hand, the SPFS device 200 is provided with a light detection means 222 that is configured to receive a fluorescence 220 that is emitted from a fluorescence substance that has labeled an analyte that has been captured by the ligand immobilized region 206 on the side of the ligand containing layer 208 of the sensor structure 210.

A light collection member 224 that is configured to collect the fluorescence 220 in an efficient manner and a wavelength selection function member 226 that is configured to remove a light that is included in other than the fluorescence 220 and that is configured to select the required fluorescence 220 only are formed between the ligand containing layer 208 and the light detection means 222.

In the case in which the SPFS device 200 is used, a ligand is affixed to the ligand immobilized region 206 formed on the metallic thin film 204, and an analyte that has been labeled by a fluorescence substance is captured by the ligand.

Moreover in this state, the excitation light 212 is applied from the light source 214 into the dielectric member 202, and the excitation light 212 is incident to the metallic thin film 204 at a resonance angle θ2, whereby a crude density wave (a surface plasmon) is generated on the metallic thin film 204.

In the case in which a crude density wave (a surface plasmon) is generated on the metallic thin film 204, a coupling of the excitation light 212 and an electronic vibration in the metallic thin film 204 occurs, thereby causing a light amount of the reflected light 216 to be reduced. Consequently, by finding out a point in which a signal is varied (a light amount is reduced) for the reflected light 216 that is received by the light receiving means 218, a resonance angle θ2 by which a crude density wave (a surface plasmon) is generated can be obtained.

Based on the phenomenon that generates the crude density wave (a surface plasmon), a fluorescence substance of the ligand immobilized region 206 on the metallic thin film 204 is excited in an efficient fashion, whereby a light amount of the fluorescence 220 that is emitted from a fluorescence substance is increased.

By receiving the increased fluorescence 220 by the light detection means 222 via the light collection member 224 and the wavelength selection function member 226, an analyte of an infinitesimal quantity and/or an extremely low concentration can be detected.

In recent years, for the SPR device 100 and the SPFS device 200, an engineering development has been actively carried out for a further accuracy improvement.

By the way, as a method for supplying a sample solution to the ligand immobilized region 106 of the SPR device 100 and the ligand immobilized region 206 of the SPFS device 200, there can be known a supply method for supplying a solution by using a flow passage for instance.

The sensor structure 300 as shown in FIG. 14 is provided with a ligand immobilized region 306 on the metallic thin film 304 on the way of a horizontal type flow passage 308. In the case in which a sample solution 310 that includes a specific substance (an analyte) in the horizontal type flow passage 308 is sent after a ligand is affixed to the ligand immobilized region 306 in the horizontal type flow passage 308, the analyte is captured by the ligand immobilized region 306. A symbol 302 in the figure represents a dielectric member.

The sensor structure 300 that is provided with such the horizontal type flow passage 308 is designed to generate a reaction of a specific substance at any point of the ligand immobilized region 306 by circulating a sample solution 310 by using a unidirectional solution sending pump or by sending the solution in a reciprocating manner by using a reciprocated solution sending pump.

On the other hand, as another method for supplying a sample solution to the ligand immobilized region 106 of the SPR device 100, there can be known a supply method for storing a sample solution for instance.

For the sensor structure 400 that is disclosed in the Patent Literature 1, a well member 408 that is provided with a plurality of through holes 410 is formed on a ligand immobilized region 406 on a metallic thin film 404 as shown in FIG. 15, and a sample solution 412 is supplied and stored in each of the through holes 410. By this configuration, an analyte is captured by the ligand immobilized region 406 in the through hole 410.

For this method, it is not necessary that a solution sending pump is prepared like a method in which a solution sending is carried out by using a flow passage. Consequently, this method has the advantage of being able to simplify a structure as compared with the case in which a flow passage is used.

PRIOR ART DOCUMENTS

Patent Literature

[Patent Literature 1]
Japanese Patent Publication No. 3743541

SUMMARY OF INVENTION

Problems to be Solved by the Invention

In the case in which the sensor structure that is provided with a well member as described above is used for the SPFS device and a sample solution is stored to carry out a fluorescence measurement, it is thought that a structure can be simplified and a manufacturing cost can be suppressed similarly to the SPR device.

However, in the case of a method for storing a sample solution by using a well member, it is hard to generate a flow of a sample solution in a through hole of a well member. In the case in which a specific substance that is to be a detection target is an infinitesimal quantity moreover, a specific substance cannot be captured by a ligand of the ligand immobilized region in a certain manner in some cases.

In particular, the above issue is a fatal problem for the SPFS device in which a higher degree of precision is required as compared with the SPR device. This problem is one of causes in which the sensor structure that is provided with a well member is difficult to be used for the SPFS device.

The present invention was made in consideration of such conditions, and an object of the present invention is to provide a surface plasmon-field enhanced fluorescence measurement device and a fluorescence detection method using the surface plasmon-field enhanced fluorescence measurement device in which a specific substance can be detected with a high degree of accuracy even in the case in which a sensor structure that is provided with a well member and a manufacturing cost can be suppressed by simplifying a structure as compared with a solution sending method using a flow passage.

Means for Solving the Problems

The present invention was made in order to solve the problems of the conventional art described above and achieve the purpose.

A surface plasmon-field enhanced fluorescence measurement device in accordance with the present invention is characterized by comprising:

a sensor structure that is configured from a sensor member that is provided with a dielectric member, a metallic thin film formed on the dielectric member, and a ligand immobilized region formed on the metallic thin film, and a well member that is affixed onto the sensor member and that is provided with a through hole at a position that is corresponded to the ligand immobilized region; and a device body that is provided with at least a light source for applying excitation light to the metallic thin film of the sensor structure, and a light detection means for exciting a fluorescent substance held in the ligand immobilized region on the metallic thin film by applying the excitation light to the metallic thin film from the light source to enhance an electric field on the metallic thin film, and detecting fluorescence that has been excited, wherein the sensor structure is configured so as to be used attachably to and detachably from the device body or so as to be used while being affixed to the device body, and the application position of the excitation light is set in such a manner that the center of the optical axis of the excitation light is located at a position a predetermined distance away from the position of the center of gravity of a bottom surface region that is defined by the through hole of the well member of the sensor structure.

A specific substance can be detected with a high degree of accuracy in the case in which application position of the excitation light is modified as described above. In addition, a sensor structure that is provided with a well member does not require a solution sending means such as a flow passage and a pump, thereby suppressing a manufacturing cost in accordance with a device.

A fluorescence detection method in accordance with the present invention is characterized by comprising at least:

a step of capturing an analyte by a ligand that is affixed to a ligand immobilized region of a sensor structure that is configured from a sensor member that is provided with a dielectric member, a metallic thin film formed on the dielectric member, and a ligand immobilized region formed on the metallic thin film, and a well member that is affixed onto the sensor member and that is provided with a through hole at a position that is corresponded to the ligand immobilized region, and labeling the analyte by a fluorescent substance;

a step of exciting the fluorescent substance by applying the excitation light to the metallic thin film of the sensor structure from the side of the dielectric member in the state in which the analyte is labeled by a fluorescent substance; and a step of detecting fluorescence that has been excited by a light detection means, wherein the excitation light is applied in such a manner that the center of the optical axis of the excitation light is located at a position a predetermined distance away from the position of the center of gravity of a bottom surface region that is defined by the through hole of the well member of the sensor structure in the step of exciting the fluorescent substance.

By the fluorescence detection method, a specific substance can be detected with a high degree of accuracy.

The surface plasmon-field enhanced fluorescence measurement device in accordance with the present invention is characterized in that the application position of the excitation light is a position in a range from 1 to 75% away from the position of the center of gravity in the case in which a shortest distance from a position of the center of gravity of a bottom surface region that is defined by a through hole of the well member to an outer shape edge of the through hole is 100%.

The fluorescence detection method in accordance with the present invention is characterized in that the application position of the excitation light is a position in a range from 1 to 75% away from the position of the center of gravity in the case in which a shortest distance from a position of the center of gravity of a bottom surface region that is defined by a through hole of the well member to an outer shape edge of the through hole is 100% in the step of exciting the fluorescent substance.

By defining the application position of the excitation light in such a range, a specific substance can be detected with a high degree of accuracy.

The surface plasmon-field enhanced fluorescence measurement device in accordance with the present invention is characterized in that the sensor structure is used while being stirred.

The fluorescence detection method in accordance with the present invention is characterized in that the sensor structure is stirred in the step of labeling the analyte by a fluorescent substance.

In the case in which a sample solution is supplied into a through hole, an analyte can be captured by a ligand of a ligand immobilized region in a certain manner by such a stirring. Consequently, a specific substance can be detected with a high degree of accuracy.

The surface plasmon-field enhanced fluorescence measurement device in accordance with the present invention is characterized in that the through hole of the well member is provided with a reverse taper in which a diameter is decreased by degrees toward the bottom of the through hole. In the case in which such a through hole is formed, fluorescence that is generated in a radial fashion in the fluorescence detection can be collected in a certain manner. Consequently, a specific substance can be detected with a high degree of accuracy.

The surface plasmon-field enhanced fluorescence measurement device in accordance with the present invention is characterized in that a shape of the through hole of the well member is a shape that is symmetric with respect to a point.

By such a shape described above, a flow of a sample solution can easily come into being in a through hole in the case in which a sample solution is stored in a through hole, and an analyte can be captured by a ligand of a ligand immobilized region in a certain manner by such a stirring. Consequently, a specific substance can be detected with a high degree of accuracy.

The surface plasmon-field enhanced fluorescence measurement device in accordance with the present invention is characterized in that there is one kind of ligand that is affixed to the ligand immobilized region. By this configuration, one kind of an analyte can be detected.

The surface plasmon-field enhanced fluorescence measurement device in accordance with the present invention is characterized in that there is a plurality of kinds of ligands that are affixed to the ligand immobilized region. By this configuration, one sensor structure can perform an inspection in the same condition, a multiple issue inspection, a reference and so on.

The surface plasmon-field enhanced fluorescence measurement device in accordance with the present invention is characterized in that one through hole is formed in the well member. In the case in which there is one through hole that is formed as described above, a processing is easily carried out and a high accuracy of positioning in the ligand immobilized region is not required. Consequently, a manufacture of a sensor structure can be easily carried out.

The surface plasmon-field enhanced fluorescence measurement device in accordance with the present invention is characterized in that a plurality of through holes is formed in the well member. In the case in which there is a plurality of through holes that are formed as described above, one sensor structure can perform an inspection in the same condition, a multiple issue inspection, a reference and so on.

The surface plasmon-field enhanced fluorescence measurement device in accordance with the present invention is characterized by further comprising a position adjusting means that is configured to move the sensor structure and the light source in a relative manner for an adjustment.

By this configuration, in the case in which the excitation light is applied to a position a distance away from the position of the center of gravity of a bottom surface region that is defined by the through hole of the well member, an accurate position adjustment can be easily carried out.

Moreover, in the case in which a sensor structure that is provided with a plurality of through holes or a sensor structure in which a plurality of kinds of ligands is affixed is used, an inspection in the same condition, a multiple issue inspection, a reference and so on can be processed in an efficient fashion.

The surface plasmon-field enhanced fluorescence measurement device in accordance with the present invention is characterized in that a surface treatment for preventing a non-specific adsorption is applied to an inner wall surface of the through hole of the well member.

By this configuration, in the case in which a sample solution is supplied into a through hole, it is difficult that a specimen material (analyte) in a sample solution is adsorbed to an inner wall surface of the through hole. Consequently, the condition is raised in which a specific substance in a sample solution is captured in a ligand immobilized region that is located on the bottom surface of the through hole. As a result, a degree of accuracy of detection can be improved.

Advantageous Effects of Invention

In accordance with the present invention, a surface plasmon-field enhanced fluorescence measurement device and a fluorescence detection method using the surface plasmon-field enhanced fluorescence measurement device can be provided in which a specific substance can be detected with a high degree of accuracy even in the case in which a sensor structure that is provided with a well member and a manufacturing cost can be suppressed by means of a simpler structure.

DESCRIPTION OF EMBODIMENTS

An embodiment of the present invention will be described below in detail with reference to the drawings.

A surface plasmon-field enhanced fluorescence measurement device (an SPFS device) in accordance with the present invention is configured to certainly excite a fluorescent substance that labels an analyte that has been captured by a ligand that has been affixed to a ligand immobilized region and to carry out the fluorescence detection with a high sensitivity.

The term of a "surface plasmon" that is described in the present specification is used in the broad sense of the word and includes a "localized plasmon".

Moreover, a "bottom surface region that is defined by the through hole of the well member" is a region that is partitioned by an open end on the side of a metallic thin film of the through hole.

Figure 1:
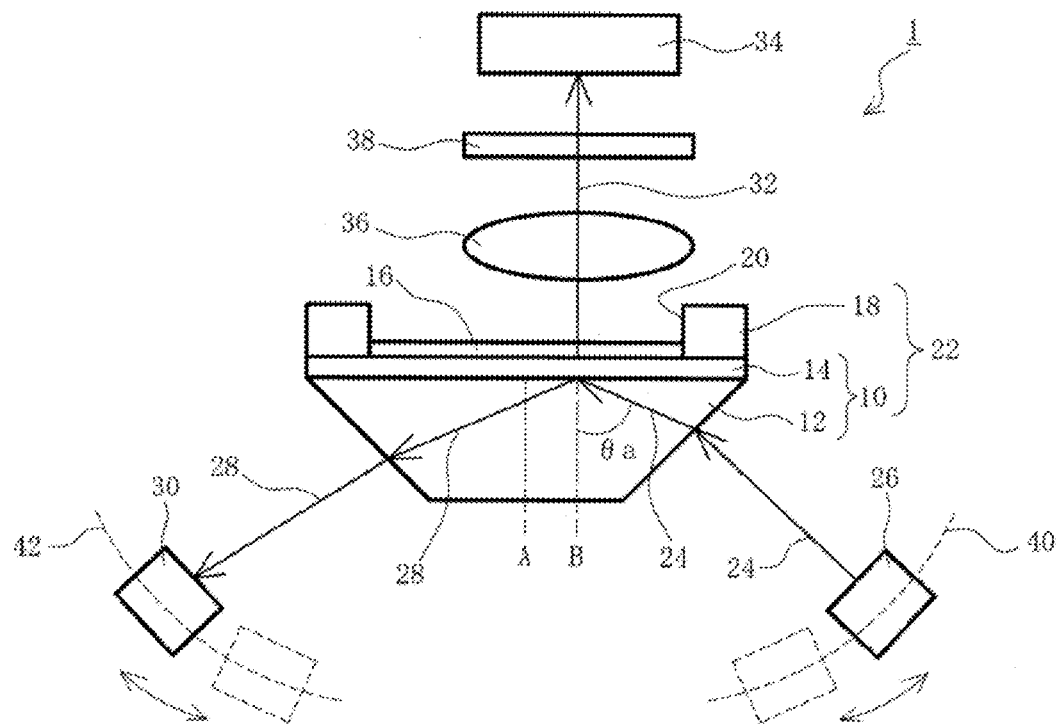
FIG. 1 is a schematic view for showing an SPFS device in accordance with the present invention.

As shown in FIG. 1, an SPFS device 1 in accordance with the present invention is provided with a sensor member 10 that is provided with a dielectric member 12, a metallic thin film 14 formed on the dielectric member 12, and a ligand immobilized region 16 that is formed on top surface of the metallic thin film 14 and that is configured to affix a ligand that is specifically adsorbed with an analyte that is a detection target. In addition, the SPFS device 1 is provided with a sensor structure 22 in which a well member 18 that is provided with a through hole 20 at a position that is corresponded to the ligand immobilized region 16 is affixed onto the sensor member 10.

Such the sensor structure 22 can be produced by forming the metallic thin film 14 on top surface of the dielectric member 12 for instance, then affixing a ligand on the entire surface of the metallic thin film 14, and affixing the well member 18 on top surface of the metallic thin film 14 in this state.

For this production method, before the well member 18 is affixed, a ligand is affixed the ligand immobilized region 16 on top surface of the metallic thin film 14. Therefore, a ligand can be prevented from being attached to an inner wall surface of the through hole 20 of the well member 18. As a result, this production method is preferable to improve the detection efficiency. Moreover, a ligand is affixed on the entire surface of the metallic thin film 14. Consequently, in the case in which a ligand is affixed, it is not necessary to use another member for restricting a fixation of a ligand to only the ligand immobilized region 16, thereby achieving a simple and easy production.

As a matter of course, it is not always necessary that a ligand is affixed on the entire surface of the metallic thin film 14. A ligand can also be affixed on a region equivalent to the ligand immobilized region 16 or a region that includes the ligand immobilized region 16 and that is slightly larger than the ligand immobilized region 16. In this case, it is preferable that a ligand is affixed on the metallic thin film 14 by using a frame member that is different from the well member 18.

As described above, it is preferable that a ligand is affixed over the entire region of the bottom face region that is defined by the through hole 20 of the well member 18 in order to prevent a non-specific adsorption and to reduce a noise.

As another production method, a ligand can also be affixed on only the metallic thin film 14 that is located on the bottom face of the through hole 20 by forming the metallic thin film 14 on top surface of the dielectric member 12, then forming the well member 18 in which a surface treatment for preventing a non-specific adsorption is applied to an inner wall surface of the through hole 20 of the well member 18 in advance, and injecting a solution that includes a ligand in the through hole 20.

As a surface treatment that is applied to an inner wall surface of the through hole 20, a publicly known processing method can be used. In the case in which a solution that includes a protein substance such as a BSA and a casein or a solution that includes a phospholipid analog synthetic polymer (NOF CORPORATION) is used, a non-specific adsorption can be prevented in an effective manner.

Figure 2:
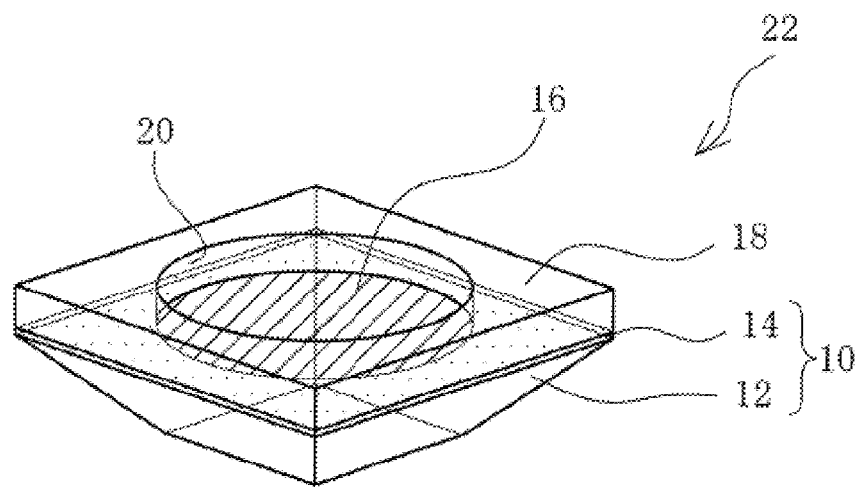
FIG. 2 is a perspective view for showing a sensor structure that is used for an SPFS device in accordance with the present invention.

For the sensor structure 22 as shown in FIG. 2, the dielectric member 12 is in a hexahedron shape with a cross sectional shape in a generally trapezoidal shape (a frustum shape of a quadrangular pyramid), and the well member 18 is configured in a rectangular shape in accordance with a shape of the dielectric member 12.

A shape of the dielectric member 12 is not restricted to a mode that is shown in FIG. 2, and can also be a pyramid shape such as a quadrangular pyramid, a circular cone, a triangular pyramid, and a polygonal pyramid or a frustum shape of a pyramid.

In the case in which the dielectric member 12 in a frustum shape of a quadrangular pyramid as shown in FIG. 2 is used, a height of the sensor structure 22 can be suppressed to be lower, thereby contributing to a downsizing of the SPFS device 1.

In addition, the SPFS device 1 is provided with a light source 26 that is configured to be incident into the dielectric member 12 and to apply an excitation light 24 toward the metallic thin film 14 and a light receiving means 30 that is configured to receive a reflected light 28 that has been applied from the light source 26 and that has been reflected on the metallic thin film 14 on the side of the dielectric member 12 of the sensor structure 22.

The light source 26 and the light receiving means 30 is provided with the position adjusting means 40 and 42 that are configured to adjust an application position and a light receiving position.

A laser light is preferable as an excitation light 24 that is applied from the light source 26. In particular, an LD laser that is provided with a wavelength in the range of 200 to 900 nm and 0.001 to 1000 mW and a semiconductor laser that is provided with a wavelength in the range of 230 to 800 nm and 0.01 to 100 mW are preferable to be used.

On the other hand, the SPFS device 1 is provided with a light detection means 34 that is configured to receive a fluorescence 32 that is generated in the ligand immobilized region 16 on the side of the well member 18 of the sensor structure 22.

As the light detection means 34, it is preferable to use a photomultiplier tube with ultrahigh sensitivity and a CCD image sensor capable of performing a multipoint measurement.

A light collection member 36 that is configured to collect a light in an efficient manner and a wavelength selection function member 38 that is configured to select only the fluorescence 32 among lights are formed between the ligand containing layer 16 and the light detection means 34 of the sensor structure 22. The device body is configured by the above components.

For the SPFS device 1 as shown in FIG. 1, the sensor structure 22 is configured so as to be used attachably to and detachably from the device body. However, this invention is not restricted to such a configuration, and the sensor structure 22 can also be used while being affixed to the device body.

As the light collection member 36, any light collection system can be used as long as it is configured to collect a fluorescence signal in an efficient manner. As a simple light collection system, a commercially available objective lens that is used for a microscope or the like can be diverted. As a magnification of an objective lens, a magnification of the range of 10- to 100-fold is preferable.

On the other hand, as the wavelength selection function member 38, an optical filter and a cut filter can be used for instance.

As an optical filter, a neutral density filter (ND filter) and a diaphragm lens can be mentioned for instance.

As a cut filter, there can be mentioned for instance a filter that is configured to remove a wide variety of noise lights such as an outside light (an illumination light outside the device), an excitation light (a transmission component of an excitation light), a stray light (a scattering component of an excitation light at each point), a scattering light of a plasmon (a scattering light that is generated by an influence of an extraneous matter that has adhered to a surface of the sensor structure 22 in the case in which an excitation light is an original source), and a self-fluorescence of an enzyme fluorescent substrate, such as an interference filter and a color filter.

As a method for detecting a fluorescence by using the SPFS device 1 that is configured as described above, in the state in which a ligand that is specifically adsorbed with an analyte that is a detection target is affixed to a ligand immobilized region 16 that is formed on top surface of the metallic thin film 14 of the sensor structure 22, a sample solution that includes an analyte that is a detection target is supplied into a through hole 20, and the sensor structure 22 is stirred.

It is preferable that a fixation of a ligand to the ligand immobilized region 16 is carried out in advance before the fluorescence detection is carried out in order to reduce a time that is required for the fluorescence detection. However, this invention is not restricted to this process, and the fixation of a ligand can also be carried out immediately before the fluorescence detection.

Moreover, after the inside of the through hole 20 is cleaned, a solution that includes a fluorescence substance that is captured by a specimen material (analyte) is supplied into the through hole 20 and is stirred. After that, the inside of the through hole 20 is cleaned again. By this process, an analyte that has been labeled by the fluorescence substance is captured by the ligand.

In this state, an excitation light 24 is applied to the metallic thin film 14 from the light source 26. In the case in which the excitation light 24 is incident to the metallic thin film 14 at a specific angle (a resonance angle (an angle that is made by the excitation light 24 and a perpendicular line of the metallic thin film 14 when an electrical field is enhanced) θa), a crude density wave (a surface plasmon) is generated on the metallic thin film 14.

In the case in which a crude density wave (a surface plasmon) is generated on the metallic thin film 14, a coupling of the excitation light 24 and an electronic vibration in the metallic thin film 14 occurs, thereby causing a signal of the reflected light 28 to be varied (a light amount is reduced). Consequently, by finding out a point in which a signal is varied (a light amount is reduced) for the reflected light 28 that is received by the light receiving means 30, a resonance angle θa by which a crude density wave (a surface plasmon) is generated can be obtained.

Based on the phenomenon that generates the crude density wave (a surface plasmon), a fluorescence substance that has been generated in the ligand immobilized region 16 on the metallic thin film 14 is excited in an efficient fashion, whereby a light amount of the fluorescence 32 that is emitted from a fluorescence substance is increased. By receiving the increased fluorescence 32 by the light detection means 34 via the light collection member 36 and the wavelength selection function member 38, an analyte of an infinitesimal quantity and/or an extremely low concentration can be detected.

As a material of the metallic thin film 14 of the sensor structure 22, the metallic thin film 14 is made of a metal of at least one kind that is selected from a group that is composed of gold, silver, aluminum, copper, and platinum, preferably gold, and more preferably an alloy of the metal. Such a metal is stable to oxidization and is suitable for the metallic thin film 14 since an electrical field enhancement caused by the crude density wave (a surface plasmon) is increased.

As a method for forming the metallic thin film 14, there can be mentioned for instance a sputtering method, a vapor deposition method (such as a resistance heating vapor deposition method and an electron beam vapor deposition method), an electrolytic plating method, and an electroless plating method. Among them, a sputtering method and a vapor deposition method are preferable since an adjustment of the condition of a thin film formation can be easily carried out.

As a thickness of the metallic thin film 14, it is preferable that a thickness of gold is in the range of 5 to 500 nm, a thickness of silver is in the range of 5 to 500 nm, a thickness of aluminum is in the range of 5 to 500 nm, a thickness of copper is in the range of 5 to 500 nm, a thickness of platinum is in the range of to 500 nm, and a thickness of an alloy of the metal is in the range of 5 to 500 nm. From the aspect of an electrical field enhancement effect, it is more preferable that a thickness of gold is in the range of 20 to 70 nm, a thickness of silver is in the range of 20 to 70 nm, a thickness of aluminum is in the range of to 50 nm, a thickness of copper is in the range of 20 to 70 nm, a thickness of platinum is in the range of 20 to 70 nm, and a thickness of an alloy of the metal is in the range of 10 to 70 nm.

In the case in which a thickness of the metallic thin film 14 is in the range described above, the thickness is suitable since the crude density wave (a surface plasmon) is easily generated. For the metallic thin film 14 that is provided with such a thickness, a size (vertical length×horizontal length) is not restricted in particular.

As a specimen material that is used in the analyte detection, there can be mentioned for instance a blood, a blood serum, a blood plasma, urine, a nasal passage fluid, a saliva, a feces, and a body cavity fluid (such as a spinal fluid, an ascites fluid, and a pleural effusion).

As an analyte that is included in a specimen material, there can be mentioned for instance a nucleic acid (single-stranded or double-stranded DNA, RNA, polynucleotide, oligonucleotide, and PNA (peptide nucleic acid), and nucleoside, nucleotide, and a modified molecule thereof), a protein substance (such as polypeptide and oligopeptide), an amino acid (including a modified amino acid), saccharide (such as oligosaccharide, polysaccharide, and a sugar chain), lipid, a modified molecule thereof, and a complex thereof. More specifically, an analyte can also be a carcinoembryonic antigen such as an AFP ($\alpha$ fetoprotein), a tumor marker, a signal transducer, and a hormone, and is not restricted in particular.

Moreover, a fluorescence substance is not restricted in particular as long as the fluorescence substance is a substance that is excited by an application of a predetermined excitation light 24 or a utilization of an electrical field effect and that emits a fluorescence 32. The fluorescence 32 that is described in the present specification includes a wide variety of emissions of lights such as phosphorescence.

As the dielectric member 12, a wide variety of inorganic substances, natural polymers, and synthetic polymers that are optically transparent can be used. From the aspect of the chemical stability, manufacturing stability, and optical transparency, it is preferable that the dielectric member 12 includes silicon dioxide ($SiO_2$) or titanium dioxide ($TiO_2$).

As the well member 18, a wide variety of materials such as a synthetic resin, metal, and ceramics can be used. For instance, a through hole 20 can be formed by a machine processing.

In the case in which the well member 18 is affixed onto the sensor member 10, it is preferable to use an adhesive agent, a matching oil, and a transparent adhesive sheet that are provided with an optical refraction index that is equivalent to that of the dielectric member 12.

As a size of a through hole 20 of the well member 18, it is preferable that the through hole 20 is set to be provided with a capacity in the range of 80 to 100 μl for instance.

Such the SPFS device 1 can also be provided with an angle variable part (not shown) and a computer (not shown) that is configured to process the information that has been input to the light detection means 34 in order to adjust an optimum angle of a surface plasmon resonance (a resonance angle $\theta a$) caused by an excitation light 24 that is applied from the light source 26 to the metallic thin film 14.

For the angle variable part (not shown), it is preferable that the light receiving means 30 and the light source 26 are synchronized with each other in order to obtain the attenuated total reflection (ATR) condition by using a servomotor, an angle modification in the range of 45 to 85° is enabled, and a resolution performance is at least 0.01°.

Figure 3:
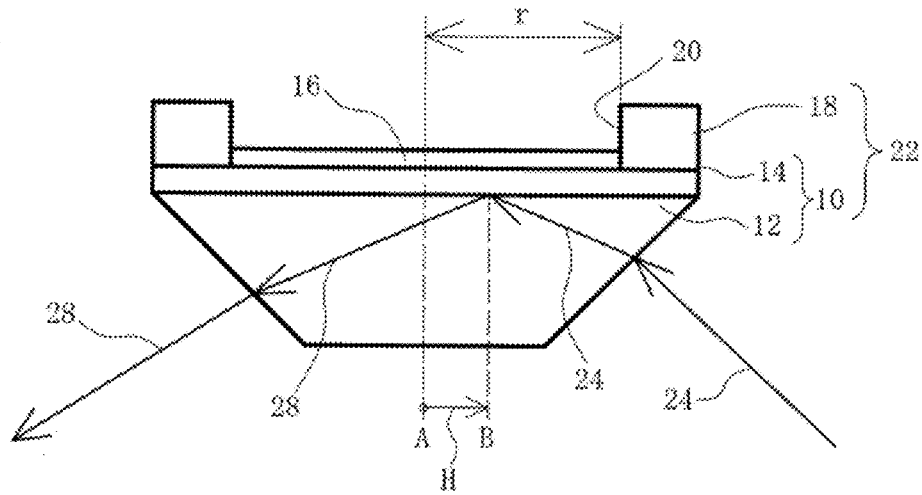
FIG. 3 is a schematic view for illustrating an application position of an excitation light for a sensor structure that is used for an SPFS device in accordance with the present invention.
Figure 4:
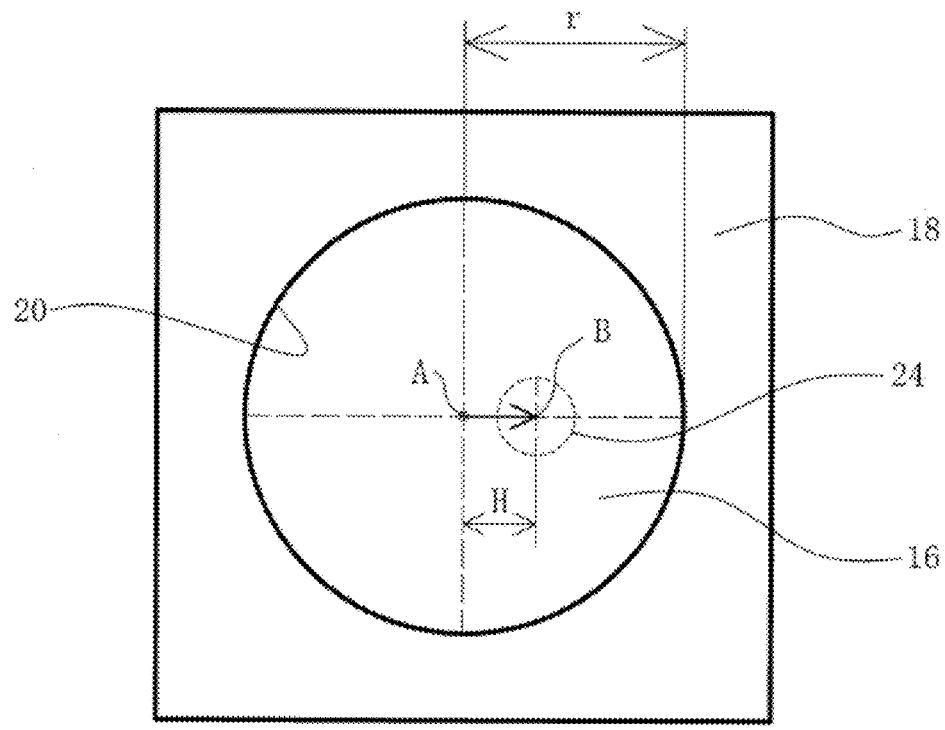
FIG. 4 is a top view for illustrating an application position of an excitation light for a sensor structure that is used for an SPFS device in accordance with the present invention.

For the SPFS device 1 that is provided with the above configuration in accordance with the present invention as shown in FIG. 3 and FIG. 4, the application position B of the excitation light 24 that is applied from the light source 26 to the metallic thin film 14 is set in such a manner that the center of the optical axis of the excitation light 24 is located at a position a predetermined distance H away from the position A of the center of gravity of a bottom surface region that is defined by the through hole 20 of the well member 18 in the case in which the fluorescence 32 that has been generated in the ligand immobilized region 16 is excited. A symbol r in the figure represents a shortest distance from the position A of the center of gravity of a bottom surface region that is defined by the through hole 20 to an outer shape edge of the through hole 20.

In the case in which the application position of the excitation light 24 is moved, it is preferable that the light source 26 is moved by using the position adjusting means 40 that has been described earlier. However, the sensor structure 22 can also be configured to be moved. The configuration of the present invention is not restricted in particular as long as the light source 26 and the sensor structure 22 can be moved to each other in a relative manner.

For the SPFS device 1 described above in accordance with the present invention, in such a manner that a specimen material (an analyte) is captured by the ligand that has been affixed in the ligand immobilized region 16 in a certain manner, after a sample solution that includes a specimen material is supplied into the through hole 20 of the well member 18, the sensor structure 22 is stirred.

For this stirring method, a stirring by a circular motion is preferable. This stirring method can be carried out by using a specific stirring device (not shown) for instance.

In the case in which the sensor structure 22 is stirred by a circular motion, a sample solution is moved in a circular pattern in the through hole 20 of the well member 18. At this time, a distribution of a reaction amount of a ligand and an analyte in the ligand immobilized region 16 has been researched by dyeing the ligand immobilized region 16 by using a gold colloid after the stirring. As a result, it has been confirmed that points of a high reaction amount are distributed in a doughnut shape from the position A of the center of gravity of a bottom surface region that is defined by the through hole 20 of the well member 18 as a point of origin.

Figure 5:
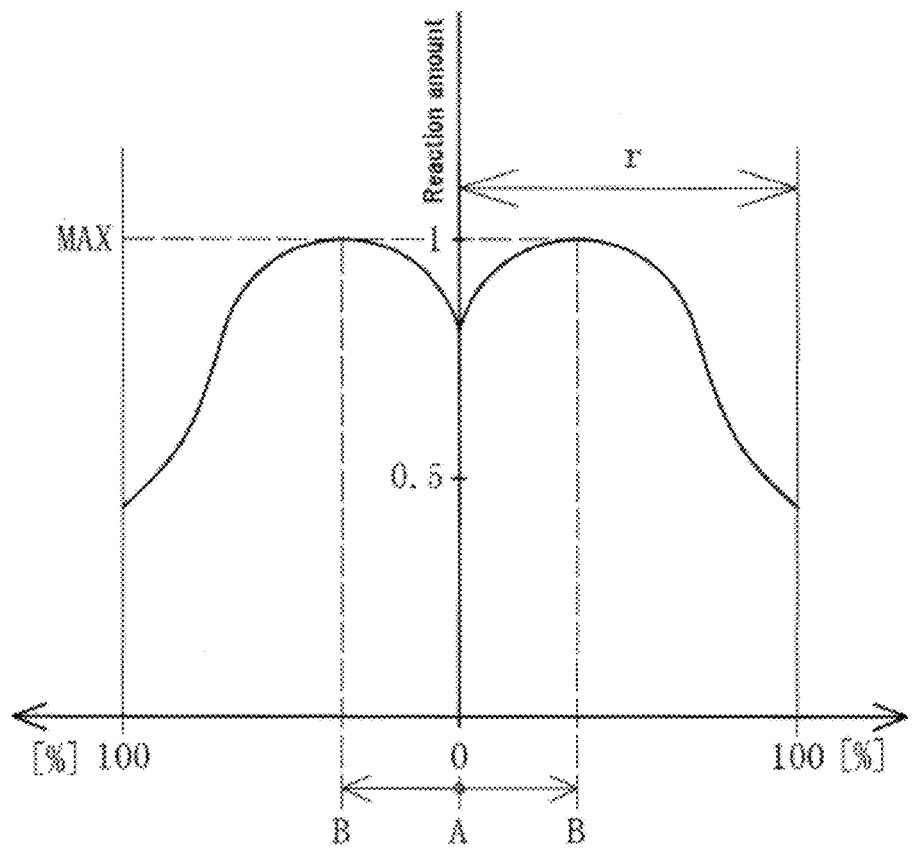
FIG. 5 is a graph for showing a distribution of a reaction amount of a ligand containing layer that is located in a through hole of a well member for a sensor structure that is used for an SPFS device in accordance with the present invention.

In the case in which the distribution of a reaction amount is indicated by a graph, it is found out that a value of a reaction amount is highest at a position B a predetermined distance away from the position A of the center of gravity of a bottom surface region that is defined by the through hole 20 of the well member 18 as shown in FIG. 5.

Consequently, the present inventors have found out that the detection efficiency of the fluorescence 32 can be improved in an effective manner by setting the application position B of the excitation light 24 to be aligned to a position in which a value of a reaction amount is highest.

Moreover, it is thought that the distribution of a reaction amount is different in the case in which the measurement conditions such as a size of the through hole 20 and a king of a ligand are different. The present inventors have found out that a value of a reaction amount is basically high at a position in a range from 1 to 75% away from the position A of the center of gravity in the case in which a shortest distance r from the position A of the center of gravity of a bottom surface region of the through hole 20 to an outer shape edge of the through hole 20 is 100%.

Consequently, the detection efficiency of the fluorescence 32 can be improved in an effective manner by setting the application position of the excitation light 24 to be in this range in advance. However, a movement range of the application position of the excitation light 24 is a range in which a diameter of an optical axis of the excitation light 24 falls within the through hole 20.

For the SPFS device 1 in accordance with the present invention as described above, the distribution of a reaction amount after the stirring of the sensor structure 22 is researched in advance, and the application position of the excitation light 24 is set to be a position in which a value of a reaction amount is highest. By this configuration, the detection efficiency of the fluorescence 32 can be improved in an effective manner.

Figure 14:
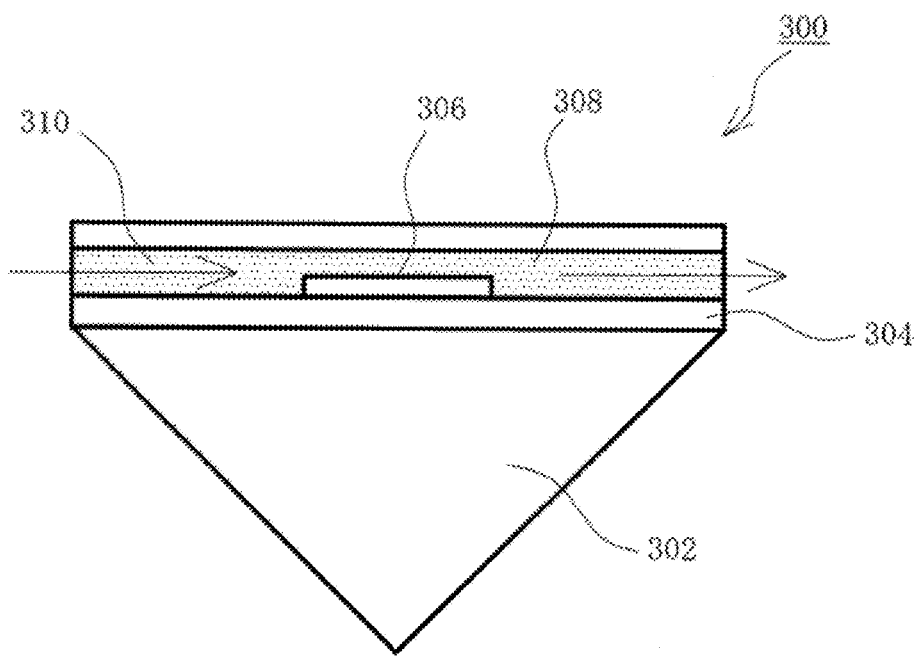
FIG. 14 is a schematic view for illustrating a supply method using a flow passage as a method for supplying a sample solution to a ligand immobilized region for a conventional sensor structure.
Figure 15:
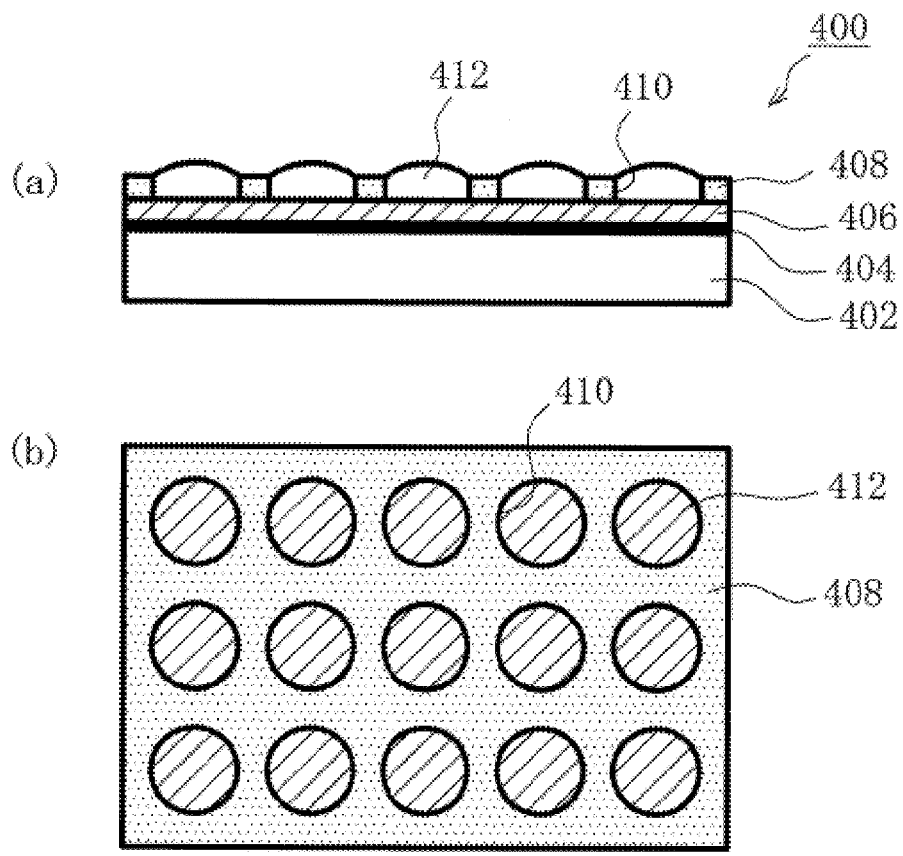
FIG. 15 is a schematic view for illustrating a supply method using a well member as a method for supplying a sample solution to a ligand immobilized region for a conventional sensor structure.

Moreover, the sensor structure 22 that is used for the SPFS device 1 in accordance with the present invention is provided with the well member 18. Consequently, it is not necessary that a solution sending means such as a pump is prepared like the sensor structure 300 of a flow passage type as shown in FIG. 14. As a result, this configuration has the advantage of being able to simplify a structure and a manufacturing cost can be suppressed.

Figure 6:
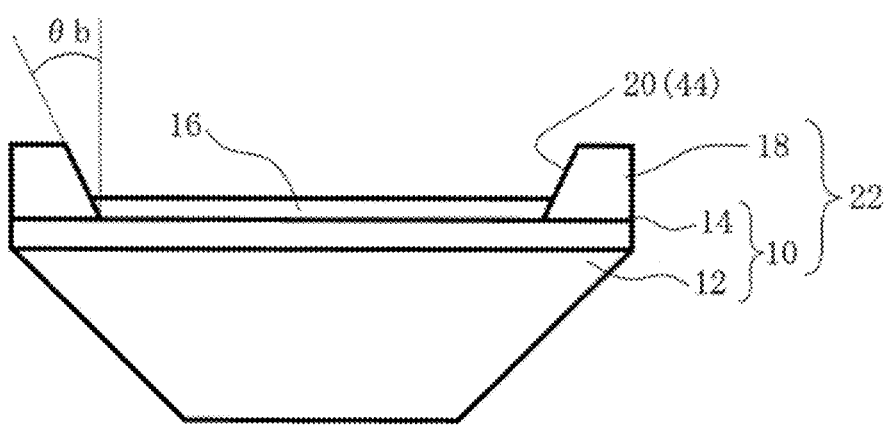
FIG. 6 is a schematic view for illustrating a reverse taper that is provided in a through hole of a well member for a sensor structure that is used for an SPFS device in accordance with the present invention.

For the sensor structure 22 that is used for the SPFS device 1 that has been described above, the through hole 20 of the well member 18 is straight. However, the through hole 20 of the well member 18 can also be provided with a reverse taper 44 in which a diameter is decreased by degrees toward the bottom of the through hole 20 as shown in FIG. 6.

By means of the above configuration, the fluorescence 32 that is generated from a fluorescence substance is diffused in a radial fashion, and the fluorescence 32 that has been diffused can be collected by the light detection means 34 in an efficient fashion.

It is preferable that an inclination angle θb of the reverse taper 44 is larger than 0° and is equal to or less than 45° in order to increase the collection efficiency.

Figure 7:
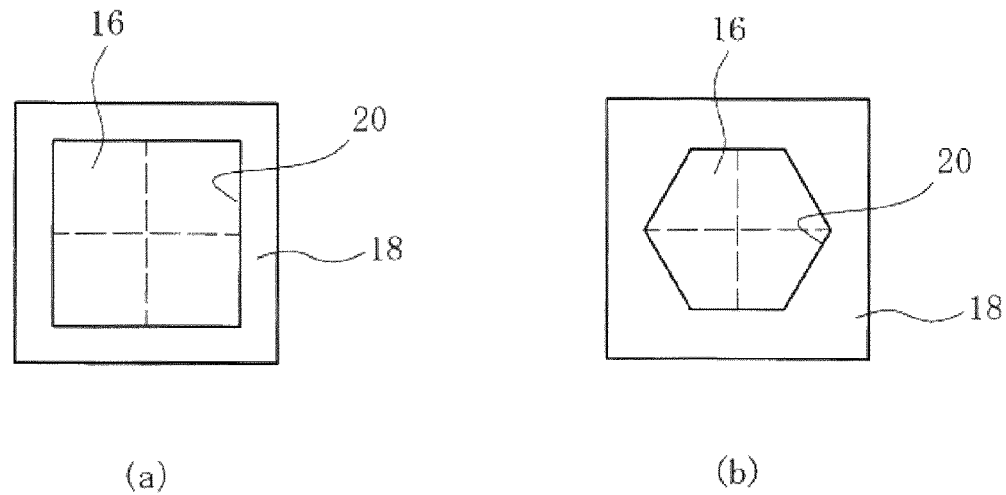
FIG. 7 is a top view for illustrating a shape of a through hole of a well member for a sensor structure that is used for an SPFS device in accordance with the present invention.

A shape of the through hole 20 is not restricted to a circular shape like the present embodiment, and can also be shape of an ellipse or a triangular shape. However, in the case in which the shape of the through hole 20 is a shape that is symmetric with respect to a point such as a quadrangular shape as shown in FIG. 7(a) or a hexagonal shape as shown in FIG. 7(b), a reaction distribution preferably appears in a prominent fashion when a stirring is carried out.

Even in the case of the through hole 20 that is provided with a shape other than a circular shape, it is preferable that a shortest distance r from the position A of the center of gravity of a bottom surface region of the through hole 20 to an outer shape edge of the through hole 20 is set to be 100% and the application position of the excitation light 24 is defined.

Figure 8:
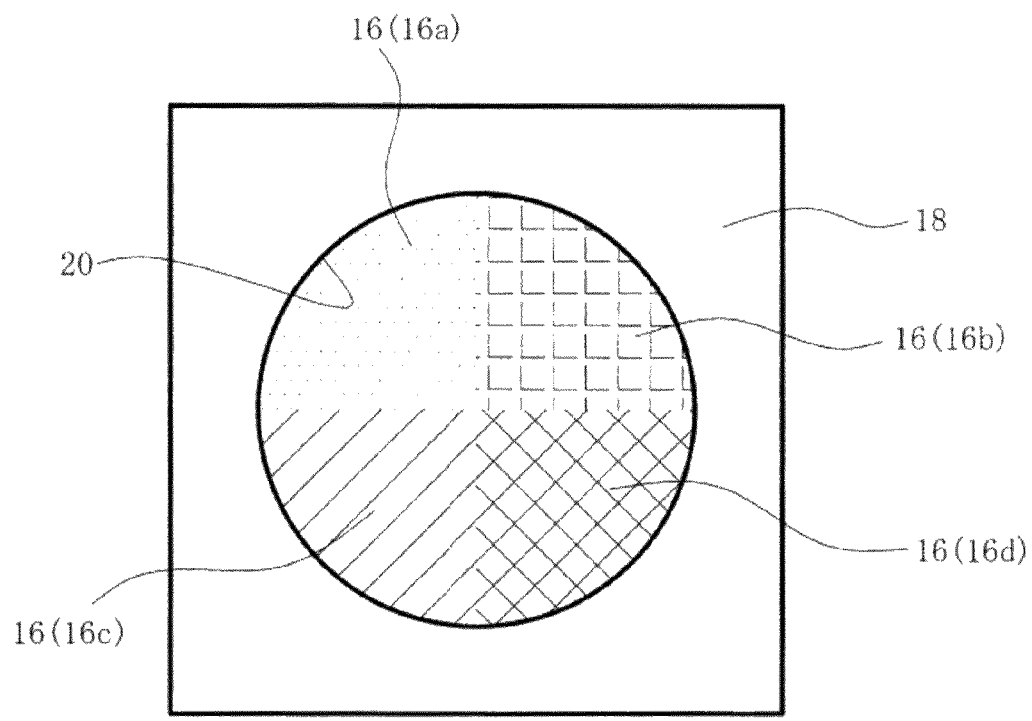
FIG. 8 is a top view for illustrating a state in which a plurality of kinds of ligands is affixed to the ligand immobilized region that is located in one through hole for a sensor structure that is used for an SPFS device in accordance with the present invention.

As shown in FIG. 8 moreover, there also can be a plurality of kinds of ligands 16a to 16d that are affixed to the ligand immobilized region 16 to one through hole 20.

Figure 9:
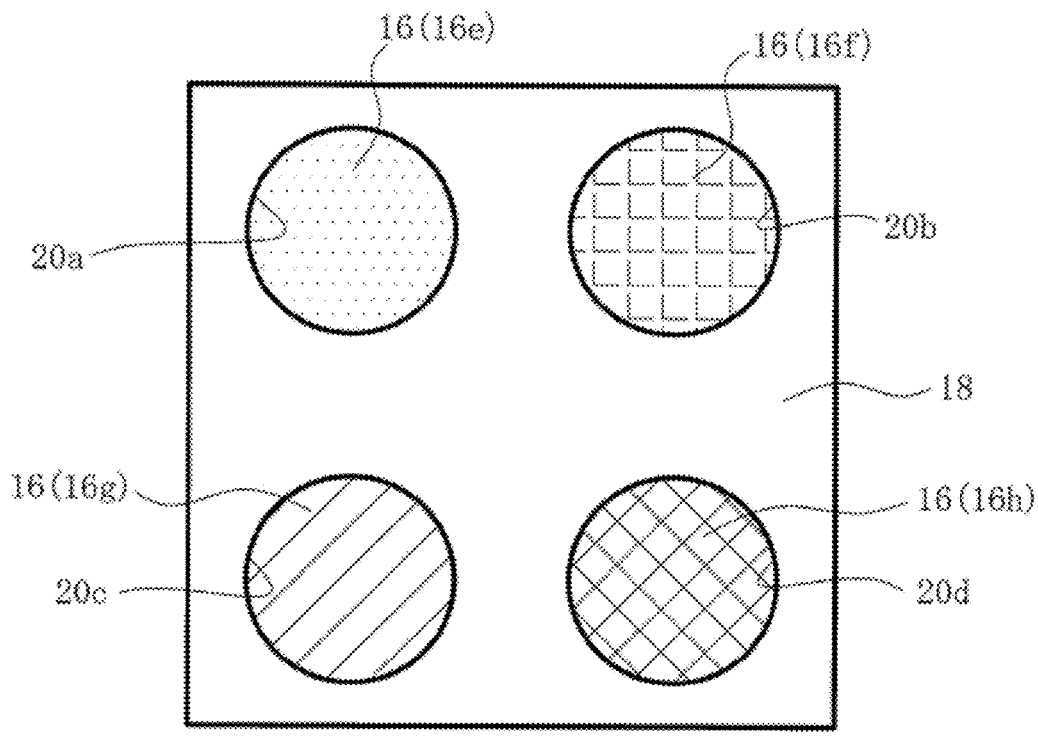
FIG. 9 is a top view for illustrating a state in which different kinds of ligands are affixed to the ligand immobilized region that is located in each through hole of a plurality of through holes for a sensor structure that is used for an SPFS device in accordance with the present invention.

As shown in FIG. 9 moreover, a well member 18 that is provided with a plurality of through holes 20 can also be used. In this case, different ligands 16e to 16h can also be affixed for every through hole 20.

In the case in which a plurality of kinds of ligands are affixed to one through hole 20 or a well member 18 that is provided with a plurality of through holes 20 is used, the fluorescence detection can be carried out without a hindrance by separately forming a movement means (not shown) in such a manner that the sensor structure 22 is rotated and moved against the light source 26 for instance.

Figure 10:
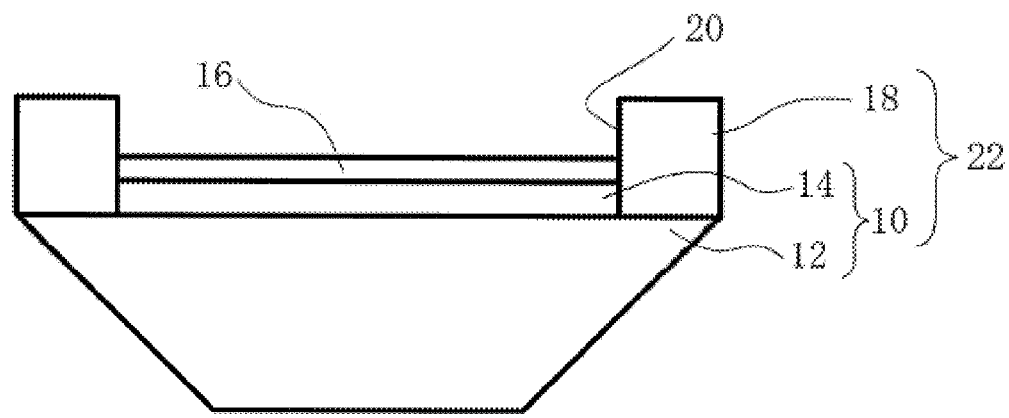
FIG. 10 is a schematic view for showing a sensor structure of another embodiment that is used for an SPFS device in accordance with the present invention.

For the sensor structure 22 as described above, the well member 18 is affixed on the metallic thin film 14. However, as shown in FIG. 10, it is also possible that the metallic thin film 14 is partially formed on the sensor structure 22 by a method such as the patterning, the ligand immobilized region 16 is then formed on the metallic thin film 14, and the well member 18 is placed on the dielectric member 12 in such a manner that the ligand immobilized region 16 and the metallic thin film 14 are fenced.

While the SPFS device 1 and a fluorescence detection method using the SPFS device in accordance with the present invention have been described above, the present invention is not restricted to the embodiments described above, and various changes, modifications, and functional additions can be thus made without departing from the scope of the present invention, such as further simplifying the configuration of the device body that has been described in the above embodiments.

EMBODIMENTS

Embodiment 1

After a metallic thin film 14 is formed on the top surface of a dielectric member 12, a ligand that is specifically adsorbed with an analyte that is a detection target is affixed on the metallic thin film 14 to form a ligand immobilized region 16.

A well member 18 that is provided with a circular through hole 20 with a diameter of φ5 mm was prepared, and the well member 18 was affixed on the metallic thin film 14 via a matching oil, whereby the sensor structure 22 was configured.

In the next place, a sample solution that includes a specimen material (analyte) was injected into the through hole 20 of the sensor structure 22, and the sensor structure 22 was set to a stirring device in which a stirring is carried out by a circular motion and was stirred.

After the sample solution was removed from the sensor structure 22 that has been stirred and the sensor structure 22 was cleaned, a specimen material (analyte) of the ligand immobilized region 16 was dyed by using a gold colloid, and the dyeing condition was confirmed by using a CCD camera. As a result, it could be confirmed that a distribution of a reaction was generated in a doughnut shape from the position A of the center of gravity of a bottom surface region that is defined by the through hole 20 of the well member 18.

Figure 11:
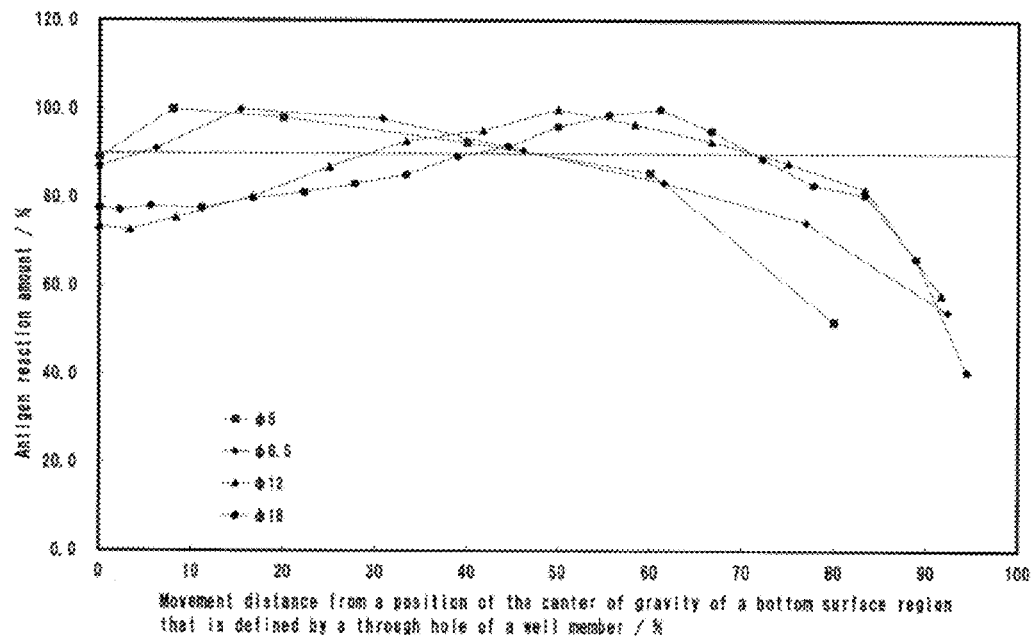
FIG. 11 is a graph for showing a distribution of a reaction amount of a ligand containing layer that is located in a through hole of a well member for a sensor structure in accordance with the embodiments 1 to 3.
Figure 12:
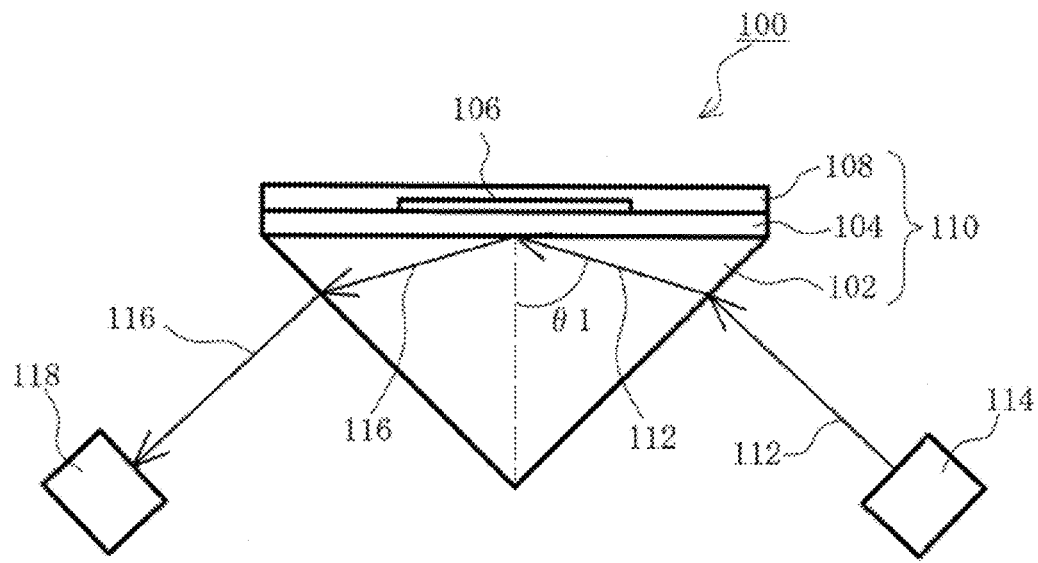
FIG. 12 is a schematic view for showing a conventional SPR device.
Figure 13:
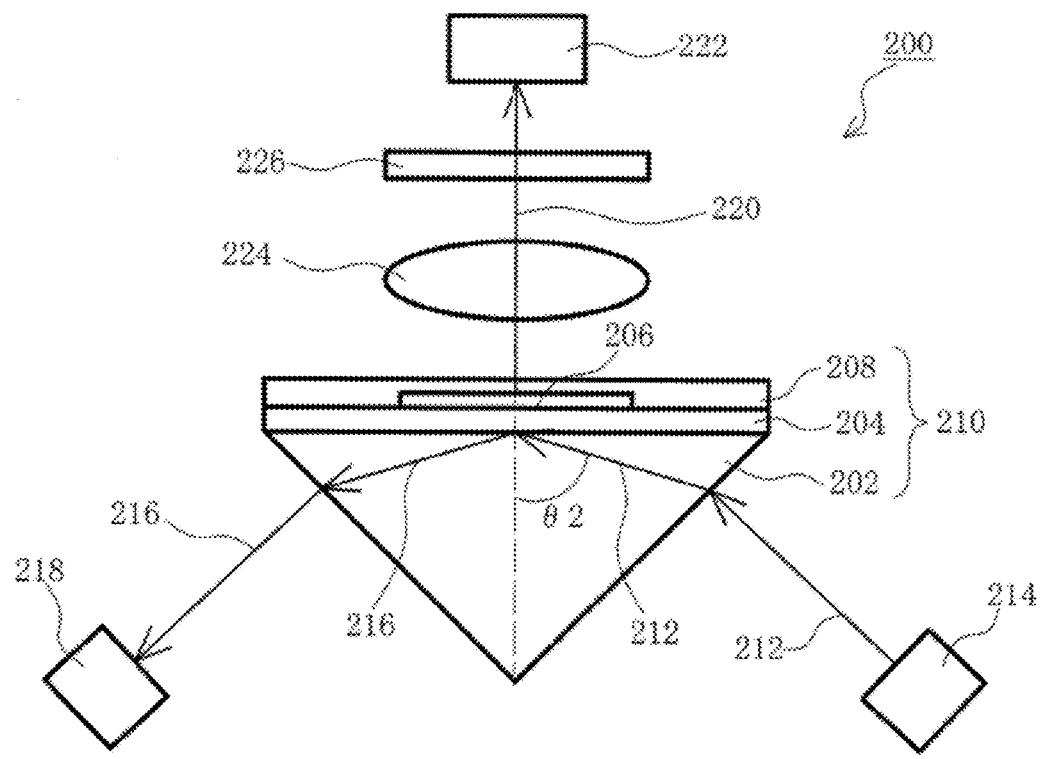
FIG. 13 is a schematic view for showing a conventional SPFS device.

The distribution of a reaction was indicated by a graph as shown in FIG. 11. In the case in which a shortest distance r from the position A of the center of gravity of a bottom surface region of the through hole 20 of the well member 18 to an outer shape edge of the through hole 20 is 100%, an X axis of the graph indicates a movement distance from the position A of the center of gravity of a bottom surface region of the through hole 20, and a Y axis of the graph indicates a reaction amount, which indicates a ratio in the case in which a maximum value of a reaction amount is 100%.

As clarified by the graph, in the case in which a shortest distance r from the position A of the center of gravity of a bottom surface region of the through hole 20 to an outer shape edge of the through hole 20 is 100%, it could be confirmed that a reaction amount indicates a maximum value at a position 8% away from the position A of the center of gravity of a bottom surface region of the through hole 20.

Embodiment 2

The sensor structure 22 was produced similarly to the embodiment 1 except for that a well member 18 that is provided with a circular through hole 20 with a diameter of $\phi$6.5 mm was used. The sensor structure 22 was then set to a stirring device in which a stirring is carried out by a circular motion and was stirred.

After the sample solution was removed from the sensor structure 22 that has been stirred and the sensor structure 22 was cleaned, a specimen material of the ligand immobilized region 16 was dyed by using a gold colloid, and the dyeing condition was confirmed by using a CCD camera. As a result, it could be confirmed that a distribution of a reaction was generated in a doughnut shape from the position A of the center of gravity of a bottom surface region that is defined by the through hole 20 of the well member 18.

The distribution of a reaction was indicated by a graph as shown in FIG. 11. It could be confirmed that a reaction amount indicates a maximum value at a position 15% away from the position A of the center of gravity of a bottom surface region of the through hole 20 of the well member 18.

Embodiment 3

The sensor structure 22 was produced similarly to the embodiment 1 except for that a well member 18 that is provided with a circular through hole 20 with a diameter of $\phi$12 mm was used. The sensor structure 22 was then set to a stirring device in which a stirring is carried out by a circular motion and was stirred.

After the sample solution was removed from the sensor structure 22 that has been stirred and the sensor structure 22 was cleaned, a specimen material of the ligand immobilized region 16 was dyed by using a gold colloid, and the dyeing condition was confirmed by using a CCD camera. As a result, it could be confirmed that a distribution of a reaction was generated in a doughnut shape from the position A of the center of gravity of a bottom surface region that is defined by the through hole 20 of the well member 18.

The distribution of a reaction was indicated by a graph as shown in FIG. 11. It could be confirmed that a reaction amount indicates a maximum value at a position 50% away from the position A of the center of gravity of a bottom surface region of the through hole 20 of the well member 18.

Embodiment 4

The sensor structure 22 was produced similarly to the embodiment 1 except for that a well member 18 that is provided with a circular through hole 20 with a diameter of $\phi$18 mm was used. The sensor structure 22 was then set to a stirring device in which a stirring is carried out by a circular motion and was stirred.

After the sample solution was removed from the sensor structure 22 that has been stirred and the sensor structure 22 was cleaned, a specimen material of the ligand immobilized region 16 was dyed by using a gold colloid, and the dyeing condition was confirmed by using a CCD camera. As a result, it could be confirmed that a distribution of a reaction was generated in a doughnut shape from the position A of the center of gravity of a bottom surface region that is defined by the through hole 20 of the well member 18.

The distribution of a reaction was indicated by a graph as shown in FIG. 11. It could be confirmed that a reaction amount indicates a maximum value at a position 61% away from the position A of the center of gravity of a bottom surface region of the through hole 20 of the well member 18.

A size of the through hole 20 of the embodiments 1 to 4 is basically in the range of a minimum size to a maximum size of the through hole 20 of the well member 18 that is available in the market. Consequently, from the results of the embodiments 1 to 4, even in the case in which a size of the through hole 20 of the well member 18 is modified, it can be confirmed that a basically satisfactory reaction is generated as long as the application position of the excitation light 24 is set to a position in which a movement distance from the position A of the center of gravity of a bottom surface region that is defined by the through hole 20 of the well member 18 is in the range of 1 to 75%.

REFERENCE SIGNS LIST

1: Surface plasmon-field enhanced fluorescence measurement device (SPFS device)
10: Sensor member
12: Dielectric member
14: Metallic thin film
16: Ligand immobilized region
16a to 16h: Ligands
18: Well member
20: Through hole
20a to 20d: Through holes
22: Sensor structure
24: Excitation light
26: Light source
28: Reflected light
30: Light receiving means
32: Fluorescence
34: Light detection means
36: Light collection member
38: Wavelength selection function member
40: Position adjusting means
42: Position adjusting means 44: Reverse taper
θa: Resonance angle
θb: Inclination angle of a reverse taper
A: Position of the center of gravity of a bottom surface region that is defined by a through hole of a well member
B: Application position of an excitation light that is applied from a light source to a metallic thin film
H: Separation distance (predetermined distance)
r: Shortest distance from a position of the center of gravity of a bottom surface region of a through hole to an outer shape edge of a through hole
100: Surface plasmon resonance device (SPR device)
102: Dielectric member
104: Metallic thin film
106: Ligand immobilized region
108: Ligand containing layer
110: Sensor structure
112: Excitation light
114: Light source
116: Reflected light
118: Light receiving means
θ1: Resonance angle
θ2: Resonance angle
200: Surface plasmon-field enhanced fluorescence measurement device (SPFS device)
202: Dielectric member
204: Metallic thin film
206: Ligand immobilized region
208: Ligand containing layer
210: Sensor structure
212: Excitation light
214: Light source
216: Reflected light
218: Light receiving means
220: Fluorescence
222: Light detection means
224: Light collection member
226: Wavelength selection function member
300: Sensor structure
302: Dielectric member
304: Metallic thin film
306: Ligand immobilized region
308: Horizontal type flow passage
310: Sample solution
400: Sensor structure
402: Dielectric member
404: Metallic thin film
406: Ligand immobilized region
408: Well member
410: Through hole
412: Sample solution

The invention claimed is:

1. A surface plasmon-field enhanced fluorescence measurement device comprising:
    a sensor structure that is configured from a sensor member that is provided with a dielectric member, a metallic thin film formed on the dielectric member, and a ligand immobilized region formed on the metallic thin film, and a well member that is affixed onto the sensor member and that is provided with a through hole for storing a sample solution at a position that is corresponded to the ligand immobilized region; and
    a device body that is provided with at least a light source for applying excitation light to the metallic thin film of the sensor structure, and a light detection means for exciting a fluorescent substance held in the ligand immobilized region on the metallic thin film by applying the excitation light to the metallic thin film from the light source to enhance an electric field on the metallic thin film, and detecting fluorescence that has been excited,
    wherein the sensor structure is configured so as to be used attachably to and detachably from the device body or so as to be used while being affixed to the device body,
    the surface plasmon-field enhanced fluorescence measurement device further comprising a position adjusting means that is configured to move the sensor structure and the light source in a relative manner for an adjustment of the application position of the excitation light that is set in such a manner that the center of the optical axis of the excitation light is located at a position a predetermined distance away from the position of the center of gravity of a bottom surface region that is defined by the through hole of the well member of the sensor structure.

2. The surface plasmon-field enhanced fluorescence measurement device as defined in claim 1, wherein the application position of the excitation light is a position in a range from 1 to 75% away from the position of the center of gravity in the case in which a shortest distance from a position of the center of gravity of a bottom surface region that is defined by a through hole of the well member to an outer shape edge of the through hole is 100%.

3. The surface plasmon-field enhanced fluorescence measurement device as defined in claim 1, wherein the sensor structure is used while being stirred.

4. The surface plasmon-field enhanced fluorescence measurement device as defined in claim 1, wherein the through hole of the well member is provided with a reverse taper in which a diameter is decreased by degrees toward the bottom of the through hole.

5. The surface plasmon-field enhanced fluorescence measurement device as defined in claim 1, wherein a shape of the through hole of the well member is a shape that is symmetric with respect to a point.

6. The surface plasmon-field enhanced fluorescence measurement device as defined in claim 1, wherein there is one kind of ligand that is affixed to the ligand immobilized region.

7. The surface plasmon-field enhanced fluorescence measurement device as defined in claim 1, wherein there is a plurality of kinds of ligands that are affixed to the ligand immobilized region.

8. The surface plasmon-field enhanced fluorescence measurement device as defined in claim 1, wherein one through hole is formed in the well member.

9. The surface plasmon-field enhanced fluorescence measurement device as defined in claim 1, wherein a plurality of through holes is formed in the well member.

10. The surface plasmon-field enhanced fluorescence measurement device as defined in claim 1, wherein a surface treatment for preventing a non-specific adsorption is applied to an inner wall surface of the through hole of the well member.

11. A fluorescence detection method comprising at least:
    a step of capturing an analyte by a ligand that is affixed to a ligand immobilized region of a sensor structure that is configured from a sensor member that is provided with a dielectric member, a metallic thin film formed on the dielectric member, and a ligand immobilized region formed on the metallic thin film, and a well member that is affixed onto the sensor member and that is provided with a through hole for storing a sample solution at a position that is corresponded to the ligand immobilized region, and labeling the analyte by a fluorescent substance;

a step of exciting the fluorescent substance by applying the excitation light to the metallic thin film of the sensor structure from the side of the dielectric member in the state in which the analyte is labeled by a fluorescent substance; and a step of detecting fluorescence that has been excited by a light detection means, wherein the sensor structure and a light source for applying the excitation light are moved in a relative manner to allow the excitation light to be applied in such a manner that the center of the optical axis of the excitation light is located at a position a predetermined distance away from the position of the center of gravity of a bottom surface region that is defined by the through hole of the well member of the sensor structure in the step of exciting the fluorescent substance.

12. The fluorescence detection method as defined in claim 11, wherein the application position of the excitation light is a position in a range from 1 to 75% away from the position of the center of gravity in the case in which a shortest distance from a position of the center of gravity of a bottom surface region that is defined by a through hole of the well member to an outer shape edge of the through hole is 100% in the step of exciting the fluorescent substance.

13. The fluorescence detection method as defined in claim 11, wherein the sensor structure is stirred in the step of labeling the analyte by a fluorescent substance.

* * * * *